United States Patent
Reed et al.

(10) Patent No.: US 6,679,824 B1
(45) Date of Patent: Jan. 20, 2004

(54) PRODUCTS AND METHODS FOR BRACHYTHERAPY

(75) Inventors: Jay Reed, Elk Grove, IL (US); Kevin Helle, Bartlett, IL (US); Mike Rapach, Carpentersville, IL (US); Charles E. Shanks, Schaumburg, IL (US)

(73) Assignee: Medi-Physics, Inc., Arlington Heights, IL (US)

( * ) Notice: Subject to any disclaimer, the term of this patent is extended or adjusted under 35 U.S.C. 154(b) by 0 days.

(21) Appl. No.: 09/937,249

(22) PCT Filed: Apr. 28, 2000

(86) PCT No.: PCT/US00/11622

§ 371 (c)(1), (2), (4) Date: Dec. 31, 2001

(87) PCT Pub. No.: WO00/64538

PCT Pub. Date: Nov. 2, 2000

Related U.S. Application Data (60) Provisional application No. 60/131,401, filed on Apr. 28, 1999.

(30) Foreign Application Priority Data

May 24, 1999 (GB) .............................. 9912059

(51) Int. Cl.$^7$ ................................................ A61N 5/00
(52) U.S. Cl. ...................................................... 600/7
(58) Field of Search ............................ 600/1, 3, 4, 7, 600/8; 623/1.13; 424/1.61, 4.25

(56) References Cited

U.S. PATENT DOCUMENTS

| | | | | |
|---|---|---|---|---|
| 2,829,636 A | * | 4/1958 | Henschke | 600/1 |
| 4,182,750 A | * | 1/1980 | Sullivan et al. | 424/1.61 |
| 4,351,337 A | * | 9/1982 | Sidman | 424/425 |
| 4,697,575 A | * | 10/1987 | Horowitz | 600/8 |
| 4,754,745 A | * | 7/1988 | Horowitz | 600/8 |
| 4,815,449 A | | 3/1989 | Horowitz | |
| 5,199,939 A | * | 4/1993 | Dake et al. | 600/3 |
| 5,460,592 A | | 10/1995 | Langton et al. | |
| 5,713,828 A | * | 2/1998 | Coniglione | 600/7 |
| 5,873,904 A | * | 2/1999 | Ragheb et al. | 623/1.13 |
| 6,159,143 A | * | 12/2000 | Lennox | 600/4 |

FOREIGN PATENT DOCUMENTS

EP 0 466 681 A 1/1992

OTHER PUBLICATIONS

A. Van't Riet, et al. "Ultrasonically Guided Transperineal Seed Implantation of the Prostate: Modification of the Technique and Qualitative Assessment of Implants" Int. J. Radiation Oncology Biol. Phys. vol. 24, 1992 pp. 555–558.

* cited by examiner

Primary Examiner—Eric F. Winakur
Assistant Examiner—Nikita R Veniaminov
(74) Attorney, Agent, or Firm—Li Cai (57) ABSTRACT

A radioactive member for use in brachytherapy comprising an essentially stiff elongate, single stranded bioabsorbable carrier material with spaced radioactive sources disposed therein, and methods for the manufacture thereof. The radioactive members may be used in the treatment of, for example, prostate cancer.

31 Claims, 5 Drawing Sheets

PRODUCTS AND METHODS FOR BRACHYTHERAPY

This application claims the benefit of provisional application No. 60/131,401 filed Apr. 28, 1999.

This invention relates to radiotherapy. More particularly, it relates to radioactive sources for use in brachytherapy and to methods for the preparation of such sources.

Brachytherapy is a general term covering medical treatment which involves the placement of a radioactive source near a diseased tissue and may involve the temporary or permanent implantation or insertion of a radioactive source into the body of a patient. The radioactive source is thereby located in proximity to the area of the body which is being treated. This has the advantage that a high dose of radiation may be delivered to the treatment site with relatively low dosages of radiation to surrounding or intervening healthy tissue.

Brachytherapy has been proposed for use in the treatment of a variety of conditions, including arthritis and cancer, for example breast, brain, liver and ovarian cancer and especially prostate cancer in men (see for example J. C. Blasko et al., *The Urological Clinics of North America*, 23, 633–650 (1996), and H. Ragde et al., *Cancer*, 80, 442–453 (1997)). Prostate cancer is the most common form of malignancy in men in the USA, with more than 44,000 deaths in 1995 alone. Treatment may involve the temporary implantation of a radioactive source for a calculated period, followed by its removal. Alternatively, the radioactive source may be permanently implanted in the patient and left to decay to an inert state over a predictable time. The use of temporary or permanent implantation depends on the isotope selected and the duration and intensity of treatment required.

Permanent implants for prostate treatment comprise radioisotopes with relatively short half lives and lower energies relative to temporary sources. Examples of permanently implantable sources include iodine-125 or palladium-103 as the radioisotope. The radioisotope is generally encapsulated in a casing such as titanium to form a "seed" which is then implanted. Temporary implants for the treatment of prostate cancer may involve iridium-192 as the radioisotope.

Conventional radioactive sources for use in brachytherapy include so-called seeds, which are sealed containers, for example of titanium, containing the radioisotope within a sealed chamber but permitting radiation to exit through the container/chamber walls (U.S. Pat. Nos. 4,323,055 and 3,351,049). Such seeds are only suitable for use with radioisotopes which emit radiation which can penetrate the chamber/container walls. Therefore, such seeds are generally used with radioisotopes which emit γ-radiation or low-energy X-rays, rather than with β-emitting radioisotopes.

U.S. Pat. No. 4,815,449 discloses a substantially non-deflecting, linear, elongated member for insertion in tumours and made of a bioabsorbable material in the form of a needle or thin pointed cylinder with a plurality of radioactive seeds disposed therein in a predetermined array.

U.S. Pat. No. 5,460,592 discloses a method and apparatus for transporting a radioactive device. The device comprises a flexible, elongated woven or braided bio-absorbable carrier material having spaced radioactive seeds disposed therein. On heating, the carrier material holding the seeds becomes semi-rigid. A length of the semi-rigid carrier material with radioactive seeds disposed therein may then be loaded into a conventional, hollow metal dispensing needle or applicator cartridge which is used to implant the radioactive seeds into or contiguous to the treatment site, for example a tumour.

A commercial product consisting of iodine-125 seeds regularly spaced at between 0.6 and 1.2 cm centre to centre inside a braided, semi-rigid bioabsorbable suture material is available from Medi-Physics Inc. under the trade name I-125 RAPID Strand™. This product may be used to treat conditions such as head and neck cancers, including those of the mouth, lips and tongue, brain tumours, lung tumours, cervical tumours, vaginal tumours and prostate cancer.

One advantage of this type of semi-rigid carrier is that the radioactive seeds are implanted or inserted into a patient with a pre-determined spacing, depending on their spacing in the carrier material. The bioabsorbable material is then slowly absorbed into the patient's body to leave the spaced seeds in position. This predetermined spacing and the semi-rigid nature of the carrier aids a physician in calculating both the total radiation dose and the dose profile which will be delivered by the seeds inside a patient's body, and also aids in accurate placement of the seeds. In addition, more than one seed is implanted at once, so lessening the time taken for implantation over that required for the placement of individual loose seeds. The risk of seed migration away from the site of implantation is also reduced (Tapen et al., *Int. J. Radiation Oncology Biol. Phys.*, vol. 42(5), pages 1063–1067, 1998).

However, radioactive sources according to U.S. Pat. Nos. 4,815,449 and 5,460,592 have a number of disadvantages. The manufacturing process requires a heating step to stiffen the carrier material holding the radioactive seeds. Excessive heat may damage the carrier material, and strict control of the heating and cooling process is critical so as to change the crystalline structure of the carrier material sufficiently to cause stiffening but without causing burning. Even when stiffness is maximised within the possibilities existing within U.S. Pat. No. 5,460,592, the carrier material is not sufficiently stiff to fully guard against jamming of the carrier within the dispensing needle or applicator when in the surgeon's hands. Jamming of the carrier within a needle is generally irreversible, so that the needle then has to be disposed of, taking into account the fact that it is now "hot" due to the presence of radioactive seeds. In addition, if the needles are not well plugged, blood and other body fluids may enter the needle and cause the bioabsorbable material to swell, again causing jamming of the carrier in the dispensing needle (Butler et al., *Radiation Oncology Investigations* 4:48–49, 1996).

The manufacturing process disclosed in U.S. Pat. No. 5,460,592 is also very labour intensive and does not lend itself easily to automation. In addition, each carrier must be visually examined after the stiffening step to ensure that the seeds are securely retained in the braided bioabsorbable material.

There is therefore a need for an improved radioactive source which does not suffer from all the disadvantages of the known sources, and which can preferably be produced using an automated manufacturing process.

In one aspect of the invention there is therefore provided a radioactive member for use in brachytherapy comprising an essentially stiff elongate, single stranded bioabsorbable carrier material with spaced radioactive sources disposed therein. The sources are preferably retained therein by deformation of the carrier material around the sources on heating, followed by subsequent cooling.

In a further aspect of the invention, there is provided a radioactive member for use in brachytherapy comprising an elongate bioabsorbable carrier material with one or more slots therein in which one or more radioactive sources are disposed in a spaced relationship. Preferably, the carrier material is essentially stiff. The slots may comprise a continuous groove or a series of discrete openings longitudinally spaced along the carrier material. Preferably, the sources are securely retained in the carrier material by heat sealing.

As a further feature of the invention there is provided a method for the production of a radioactive member for use in brachytherapy comprising an elongate, bioabsorbable carrier material with spaced radioactive sources disposed therein, said method comprising the steps of:

a) providing an elongate preferably essentially stiff and preferably single stranded bioabsorbable carrier material, b) providing a plurality of radioactive sources, c) heating the radioactive sources to a temperature above the melting or softening temperature of the carrier material, d) placing the heated sources sequentially or concurrently onto the carrier material in a predetermined pattern whereby the carrier material melts or deforms around each source, and e) cooling the carrier material such that it solidifies or hardens about each source so as to securely retain each source in place.

In an alternative embodiment of the method, in steps c) and d), the carrier material may itself be at an elevated temperature (at which it does not lose its integrity), for example following extrusion, and the sources then placed onto the material such that they are held in place as it cools. In such a method, the sources may be cold or may themselves also be heated.

In step d), an external force may also optionally be applied to deform or to further deform the carrier material around the source. For example, heated plates may be applied to the exterior of the carrier material to further melt the carrier material around the source to hold the source in place.

The carrier material may be any non-toxic, biocompatible, bioabsorbable material or a mixture of such materials. As used herein, a bioabsorbable material is any material of which a substantial portion will be metabolized within a patient's body and ultimately eliminated therefrom. Suitable bioabsorbable materials include poly(glycolic acid) (PGA) and poly(lactic acid) (PLA), polyester amides of glycolic or lactic acids such as polymers and copolymers of glycolate and lactate, polydioxanone and the like. Such materials are more fully described in U.S. Pat. No. 5,460,592 which is hereby incorporated by reference. Suitable commercially available polymers include polyglycaprone 25(MONCRYL™), polyglactin 910 (VICRYL™) and polydioanone (PDS II), all available from Ethicon, Inc. of New Jersey, U.S.A..

Other suitable bioabsorbable polymers and polymer compositions that may be used in this invention are described in the following patents which are hereby incorporated by reference: U.S. Pat. No. 4,052,988 which discloses compositions comprising extruded and oriented filaments of polymers of p-dioxanone and 1,4-dioxepan-2-one; U.S. Pat. No. 3,839,297 which discloses compositions comprising poly [L–lactide-co-glycolide] suitable for use as absorbable sutures; U.S. Pat. No. 3,297,033 which discloses the use of compositions comprising polyglycolide homopolymers as absorbable sutures; U.S. Pat. No. 2,668,162 which discloses compositions comprising high molecular weight polymers of glycolide with lactide; U.S. Pat. No. 2,703,316 which discloses compositions comprising polymers of lactide and copolymers of lactide with glydolide; U.S. Pat. No. 2,758,987 which discloses compositions comprising optically active homopolymers of L(–) lactide i.e. poly L-Lactide; U.S. Pat. No. 3,636,956 which discloses compositions of copolymers of L(–) lactide and glycolide having utility as absorbable sutures; U.S. Pat. No. 4,141,087 which discloses synthetic absorbable crystalline isomorphic copolyoxylate polymers derived from mixtures of cyclic and linear diols; U.S. Pat. No. 4,441,496 which discloses copolymers of p-dioxanone and 2,5-morpholinediones; U.S. Pat. No. 4,452,973 which discloses poly(glycolic acid)/poly(oxyalkylene) ABA triblock copolymers; U.S. Pat. No. 4,510,295 which discloses polyesters of substituted benzoic acid, dihydric alcohols, and glycolide and/or lactide; U.S. Pat. No. 4,612,923 which discloses surgical devices fabricated from synthetic absorbable polymer containing absorbable glass filler; U.S. Pat. No. 4,646,741 which discloses a surgical fastener comprising a blend of copolymers of lactide, glycolide, and poly(p-dioxanone); U.S. Pat. No. 4,741,337 which discloses a surgical fastener made from a glycolide-rich blend of polymers; U.S. Pat. No. 4,916,209 which discloses bioabsorbable semi-crystalline depsipeptide polymers; U.S. Pat. No. 5,264,540 which discloses bioabsorbable aromatic polyanhydride polymers; and U.S. Pat. No. 4,689,424 which discloses radiation sterilizable absorbable polymers of dihydric alcohols.

Bioabsorbable polymers and polymer compositions are especially useful when they comprise bioabsorbable fillers such as those described in U.S. Pat. No. 4,473,670 (which is incorporated by reference) which discloses a composition of a bioabsorbable polymer and a filler comprising a poly (succinimide); and U.S. Pat. No. 5,521,280 (which is incorporated by reference) which discloses bioabsorbable polymers and a filler of finely divided sodium chloride or potassium chloride. Such fillers can provide increased stiffness to bioabsorbable polymers and polymer compositions.

Poly(glycolic acid) has a melting point of either 223° C. or 233° C. (Polymer Handbook, J. Brandrup and E. H. Immergut, 3rd Edition, page VI/61). If this is used as the carrier material, then in steps c) and d) of the methods of the invention the sources and/or the carrier material should be heated to at least this temperature.

The bioabsorbable material should preferably maintain its integrity once implanted for from about 1 to 14 days. This helps to ensure that the spacing of the sources is maintained for at least a short period post-implantation. Use of the radioactive members of the invention also helps ensure proper dosimetry and minimizes source movement or shedding. Preferably the carrier material should be fully absorbed by living tissue over a total of about 70 to 120 days.

By "essentially stiff" is meant that the carrier material should have some structural integrity and be stiff enough for its proposed uses. The carrier material should be stiff enough to maintain the spacing between the radioactive sources during storage, shipment and implantation of the radioactive member. If the carrier material has melted and deformed when heated by the seeds so as to trap-the radioactive seeds in place, it should then re-stiffen when cooled. In addition, the carrier material should be formable into an elongate shape. Preferably, once in an elongate shape, the carrier material should be easy to cut using for example a scalpel or the like. Alternatively or additionally, the carrier material may be snapped at preset partially cut or indented points. The carrier material should also preferably have an appreciable shelf life without the need for any special storage or handling conditions. The carrier material should also be sterilisable by any conventional sterilisation method, such as for example using steam, dry heat, ethylene oxide, electron-beam or gamma-radiation. A preferred sterilization method is exposure to gamma-radiation.

Generally, a single stranded carrier material comprises an essentially continuous strand or length of a suitable bioabsorbable material. It may be formed by extrusion, for example in a single extrusion step, by moulding or by machining, planing or cutting. Preferably, it should have an essentially uniform cross section along a greater part of its length prior to placement of the seeds therein. As used herein, "single stranded" is not intended to cover, for example, a woven or braided material comprising a plurality of strands or filaments whether separate or joined together.

The carrier may be of any suitable cross-section, for example substantially circular, substantially circular with at least one flattened surface, or substantially polygonal, for example, square or triangular. A preferred carrier according to the invention has a substantially square cross-section, both for ease of manufacture and to limit the surface area of the carrier which will be in contact with the inside of the dispensing needle, so making jamming of the carrier within the needle due to friction between the needle and the surface of the carrier less likely. Reduced friction could also be achieved with any cross-section having at least one flat surface e.g. a substantially circular cross-section flattened at a region on the circumference to give a flat surface. Suitable carriers are substantially polygonal in shape, for example, hexagonal, octagonal, or 12 or 16-sided etc. Thus, another preferred carrier in accordance with the invention is substantially octagonal. A substantially triangular cross-section is also preferred, as it offers one less edge than a substantially square cross-section to contact the inner walls of a delivery needle device.

As the carrier material is single stranded, it has a smaller surface area than the equivalent prior art woven or braided materials. It therefore has a lower tendency to swell and cause jamming in the dispensing needle.

The surface contact between the inner surface of a needle or other delivery device and a carrier of any cross sectional shape can be further minimized by the provision of suitable surface structures on the carrier surface which contacts the delivery device. For example, in the case of a curved carrier surface, surface contact can be reduced by incorporating ridges, spheres or other protrusions in the area of the carrier surface that contacts the needle or delivery device surface. Preferably, these surface structures comprise biocompatible or biodegradable carrier material. A suitable method for forming such surface structures comprises application of a heated mould or press plate, the surface of which is configured as a negative of the structures being applied to the carrier. Upon application of the heated mould to the surface of the carrier, the carrier will flow into the cavities in the negative mould. Release of the carrier from the mould and cooling of the carrier will impart to the carrier surface a positive image, reciprocal to the negative image of the mould. Beads or bumps produced on the surface of the carrier provide reduced contact area and less friction between the carrier and a needle used as a delivery device.

Preferably, the carrier will be visible using ultrasound imaging techniques. For example, it may comprise sound reflecting particles or bubbles of gas which serve to enhance its ultrasound visibility. If the carrier is a polymer, bubbles of gas may be trapped in the polymer during the extrusion process to form a carrier, for example by blowing bubbles into the polymer as it is extruded. Alternatively, the polymer may be agitated (e.g. by sonication) prior to extrusion under a suitable gas atmosphere such that bubbles of gas are incorporated therein. Suitable gases include air, nitrogen, carbon dioxide, Freons™ and fluorocarbons such as perfluorobutane.

Alternatively, the carrier material may be subjected to a gas under pressure, for example greater than atmospheric pressure, immediately prior to extrusion such that the gas becomes dissolved into the material. Upon extrusion combined with a reduction in the pressure of gas due to warming (such as on extrusion into an ambient pressure and temperature environment), the gas will expand to form bubbles in the carrier material. Preferably, the bubbles are at or near the surface of the carrier.

The carrier can be uniformly visible or non-uniformly visible by ultrasound. For example, some regions of the carrier may be more visible by ultrasound than other regions. This can arise due to the presence of regions where clusters of sound reflecting gas bubbles or particles reside in a carrier.

The carrier may additionally or alternatively comprise particles which serve to enhance its visibility to ultrasound. Suitable particles include particles of metal (for example titanium or aluminium), glass, silica, iron oxide, sand, clay, plastics such as TEFLON™, porous uniformly-sized non-aggregated particles as described in U.S. Pat. Nos. 5,741,522 and 5,776,496 which are hereby incorporated by reference, hollow microcapsules or solid microspheres such as those disclosed in U.S. Pat. No. 5,648,095 which is hereby incorporated by reference, and microspheres of a fused sugar, a fused amino acid or of PEG (polyethylene glycol).

One advantage of using imaging-visible, for example ultrasound-visible, radioactive members of the invention in brachytherapy is that the signal and image may be read, measured and analysed by suitable computer software sufficiently quickly to allow a physician to plan real-time dosimetry. This is advantageous from a clinical view point for both patient and medical personnel. However, the members of the invention may be used in processes involving any type of dosimetry mapping that uses information obtained due to the imaging visibility of the sources.

In addition, a physician may use the same imaging technique, for example ultrasound, already in place during surgery to confirm both organ (e.g. prostate) position and size, and source placement. This could enable a physician to calculate if additional sources need to be inserted, for example in situations where the dose pattern needs to be recalculated based on the "real" position of the sources.

The overall dimensions of the carrier should be such that it will fit inside a dispensing needle or applicator cartridge. For example, if the internal diameter of a thin walled 18 gauge needle is 0.102 cm (0.040 inches), then the effective maximum diameter of the carrier is preferably less than 0.102 cm (0.040 inches), so that it can be dispensed from such needles.

The carrier can be uniformly or non-uniformly distributed cross-sectionally around the sources. For example where the sources are substantially cylindrical radioactive seeds, the shape of the cross-section of the internal surface of the carrier could, preferably be substantially round. In an alternative embodiment, the surface could be substantially square.

Any conventional radioactive seed may be used as the radioactive source. These include for example the radioactive seeds disclosed in U.S. Pat. Nos. 5,404,309, 4,784,116, 4,702,228, 4,323,055 and U.S. Pat. No. 3,351,049 which are hereby incorporated by reference. By "seed" is meant any sealed container, for example a metal container, containing or encapsulating a radioisotope. Suitable biocompatible container materials include metals or metal alloys such as titanium, gold, platinum and stainless steel; plastics such as polyesters and vinyl polymers, and polymers of polyurethane, polyethylene and poly(vinyl acetate); composites such as composites of graphite; glass such as matrices comprising silicon oxide, and any other biocompatible material. Titanium and stainless steel are preferred materials for the containers.

The radioactive source may also comprise a suitable radioisotope encapsulated within a polymer or ceramic matrix.

Typical sources are substantially cylindrical in shape and approximately 4.5 mm long with a diameter of approximately 0.8 mm.

Any radioisotope suitable for use in brachytherapy may be used in the source. Non-limiting examples include palladium-103, iodine-125, strontium-89, sulphur-35, cesium-131, gold-198, thulium-170, chromium-56, arsenic-73, yttrium-90, phosphorus-32 and mixtures thereof. Especially preferred are palladium-103 and iodine-125. More than one type of radioisotope may be present in the sources for use in the invention.

The sources are preferably disposed linearly along the longest axis of the elongate carrier material. The orientation of the sources relative to the carrier will depend on the overall size and shape of the carrier and the sources. If the sources are substantially cylindrical in shape, for example if they are conventional seeds, then they are preferably orientated with their longitudinal axes parallel to the longitudinal axis of the elongate carrier itself. Preferably, the sources are regularly spaced, for example at intervals of between 0.6 and 1.2 cm, preferably at about 1 cm intervals. A spacing of about 1 cm is preferred if the sources are to be implanted for treatment of prostate cancer. The number of sources used for any particular application will depend on the length of carrier material used. Preferably, the radioactive member is provided as a long strip which can then be cut or snapped to the desired length for a particular application by the medical staff.

Preferably, the radioactive member can be wound onto a wheel for easy dispensing. Alternatively, the member may be provided with a jig, such as the jigs disclosed in U.S. Pat. No. 5,460,592 hereby incorporated by reference.

Preferably, all the sources in one carrier will contain the same radioisotope and/or be of the same radioactive strength. If more than one type or strength of source is included in one carrier, then the different sources should be arranged in a regular pattern to allow predictable dosing.

Suitably, the carrier material will be of substantially square cross-section. Alternatively, it may be substantially round with a flat surface, polygonal (e.g. octagonal) or triangular. The carrier material will preferably have a groove or slot running along its longitudinal axis into which, during the method of the invention, the heated sources will be placed. The groove will preferably be slightly narrower than the sources to ensure that the sources are securely held therein at the end of the process.

The heated sources may be positioned manually on the carrier material in step d) of the method. Alternatively, the process may be automated and the sources positioned by a suitable machine.

As a still further feature of the invention there is provided a further method for the production of a radioactive member for use in brachytherapy comprising an elongate bioabsorbable carrier material with spaced radioactive sources disposed therein, said method comprising the steps of:

a) providing an elongate preferably single stranded bioabsorbable carrier material having a longitudinal groove or slot therein, b) providing a plurality of radioactive sources, c) placing the sources sequentially or concurrently into the groove in the carrier material such that each source is securely retained within the groove.

Preferably, the groove or slot will be diametrically opposed to a flat surface of the cross section of the carrier. For example, where the carrier is substantially round with one flattened surface, the groove or slot will be positioned opposite to this flat surface. This would allow for ease of orientation during manufacture for example, the carrier material could be orientated with the slit uppermost using the flat surface for reference so that the sources could be readily pushed into the groove.

Preferably, the groove or slot will be shaped such that once a source is placed therein it is securely retained. For example, the opening to the groove may be slightly narrower than the groove itself and the width of the source such that the source must be "clipped" into place by pushing it through the opening, and is then retained within the groove. For example, a rail or elongate lip may be formed along the long axis of the carrier inside the groove and adjacent to the opening of the groove, such that the sources, once pushed past the rail or lip, are held in place inside the groove by the rail or lip. Alternatively, a series of suitably spaced protrusions, for example knobs or tabs, may be provided just inside the opening of the groove to hold the sources in place within the groove. Preferably, the rails, lips or protrusions will be formed on both sides of the opening to the groove.

Alternatively or additionally, the sources may be held in place by a suitable biocompatible adhesive. For example, a bead of a suitable adhesive or resin could be placed in the groove with a source and then the adhesive or resin allowed to dry or a curing method used to dry it. Examples of suitable biocompatible adhesives are known in the art and include epoxy adhesives such as Tra-Bond 2105, a two part epoxy adhesive from Tra-Bond U.S. (see Chem. Eng. News, Dec. 8, 1997, 75 (49) p 40, hereby incorporated by reference); certain tyrosine- and lysine-containing heptapeptides and polypeptides as disclosed in Japanese Patent 05017499, hereby incorporated by reference; certain adhesives derived from polyphenolic proteins as disclosed in U.S. Pat. No. 5,015,677, hereby incorporated by reference; certain dental cement adhesives such as an adhesive composition comprising poly(methyl methacrylate) (PMMA) and 5% of 5-methacryloxyethyl trimellitic anhydride with partially oxidized tibutylborane as disclosed in Proc. IUPAC, I.U.P.A.C., Macromol. Symp., $28^{th}$ (1982), 395, hereby incorporated by reference; and poly(propyl methacrylate), poly(methyl methacrylate), poly(butyl methacrylate-co-ethyl methacrylate), and silicone gels (see Proc. SPIE-Int. Soc. Opt. Eng, (1998), 3258, 164–168, hereby incorporated by reference).

Alternatively or additionally, the edges of the groove can be deformed or pinched together by application of an external force, for example by applying a compression step in which the upper portion of the groove edges above the widest part of the source are contacted with one or more warmed or heated plates, baffles, flanges or diverting members which may, for example, comprise two plates oriented parallel to the axis of the carrier and substantially perpendicular to a projected radius of the source and to each other such that interaction with the groove edges produces a narrowing of the opening in the groove. This can be done after the source is placed in the groove. Alternatively, a rotating heated roller or wheel, configured to apply compression to the grooves in the above manner may be used. The edge of the roller or wheel may be concave to achieve this compression. The compression may be continuous.

Alternatively, heated plates can be used to bend the edges of the groove after a source is placed into the groove. In a grooved opening of a carrier material, the edges of the groove can be substantially perpendicular to the base of the groove. The edges of the groove can extend beyond the midpoint of the source, for example beyond the widest part of the source (such as the diameter of a substantially circular source) when viewed from the end of the source when the source is placed into the groove. With the source in the groove, heated plates, baffles, flanges or diverting members can be applied from above or beside the vertical groove edges to contact the vertical edges above the widest part of the source. The heated plates then soften the vertical groove edges and the mechanical force causes the edges to bend over the source, thereby pinching the source in place. Removal of the heated plates allows the bent edges to cool and thenceforth hold the source tightly in place in the grooved carrier.

In another embodiment, a heated rotating wheel or roller configured to apply compression to the upper edges of the groove may be used to narrow the opening of a groove after a source has been placed therein. A carrier with one or more sources in place within the groove may be fed under a heated rotating wheel or roller, such that part of the wheel or roller contacts the area of the carrier adjacent to the opening of the groove, causing it to soften or melt and so deform around the source to hold it in place. Preferably, the part of the roller or wheel contacting the carrier will have a concave surface such that the edges of the groove may be deformed or pinched together to form a completely or partially closed tube containing the sources. Contact between a given portion of the carrier and the wheel or roller can be temporary as the wheel or roller rotates. Optionally, the carrier may be constrained to bend and follow the circumference of the wheel or roller and be held under tension to stretch, compress or further form it.

The carrier may be fed under the wheel or roller in a continuous process. Optionally, the part of the wheel or roller contacting the carrier may comprise a positive or negative mould such the contact with the carrier transfers a reciprocal pattern, for example comprising ridges or bumps, to the carrier.

Rather than a continuous groove or slot, the carrier may be provided with a series of discrete openings, for example slots, along its length into which one or more sources may be placed. The sources can be held in place by suitable tabs or knobs and/or by use of a suitable adhesive or resin.

Alternatively or additionally, after loading with sources, the carrier can be encased within a suitable coating, for example of Vicryl™ braid, to hold the sources in place inside the groove or the discrete openings.

In another aspect of the invention there is provided a method for the production of a radioactive member for use in brachytherapy comprising an elongate, single stranded bioabsorbable carrier material with spaced radioactive sources disposed therein, said method comprising the steps of:

a) providing an elongate single stranded bioabsorbable carrier material having a plurality of discrete openings spaced longitudinally therein, b) providing a plurality of radioactive sources, c) placing the sources sequentially or concurrently into the openings in the carrier material such that each source is securely retained within the openings.

The use in the manufacturing processes according to the invention of a single-stranded bioabsorbable material, as opposed to the braided material in U.S. Pat. No. 5,460,592, contributes significantly to the advantages both in the manufacturing process and the final product. The braided material has been found not to be able to be stiffened fully. This may be due to the lack of long axis strands providing sufficient rigidity, or increasing the rigidity on long-axis compression. The single-stranded carrier material substantially improves the properties of the final product in these respects.

At the end of the manufacturing process, the radioactive member may be cut to suitable lengths and each length loaded separately into a jig, such as the jig disclosed in U.S. Pat. No. 5,460,592. Alternatively, the member may be wound onto a suitable wheel. The jig or wheel may then be shielded and packaged ready for shipping.

Optionally, the radioactive member will be shielded for shipping from the manufacturing site to the site of use. Preferably, after packaging, the product will be sterilized, for example by any conventional sterilisation procedure such as gamma irradiation or ethylene oxide sterilisation. The product can then be shipped from the manufacturer to the site of use as a sterile unit which, once removed from the packaging and shielding, is ready for the member to be used.

The radioactive members of the invention may be used in the treatment of a range of conditions including head and neck cancers (including those of the mouth, lips and tongue) brain tumours, lung tumours, cervical tumours, vaginal tumours and prostate cancer. They may be used as a primary treatment (for example in the treatment of prostate cancer or unresectable tumours) or for treatment of residual disease after excision of the primary tumour. They may be used concurrently with, or at the completion of, other treatment modalities, for example external beam radiation therapy, chemotherapy or hormonal therapy.

The radioactive members of the invention may be used alone or in combination with individual radioactive sources, for example seeds.

As a further aspect of the invention, there is also provided a method of treatment of a condition which is responsive to radiation therapy, for example cancer or arthritis, especially prostate cancer, which comprises the placement of a radioactive member comprising an essentially stiff elongate, single stranded bioabsorbable carrier material with spaced radioactive sources disposed therein at or adjacent the site to be treated within a patient for a sufficient period of time to deliver a therapeutically effective dose.

In a preferred embodiment, the radioactive member may be visualised using a suitable imaging technique, preferably ultrasound imaging, in connection with real-time dosimetry equipment.

The radioactive members of the invention may be administered to a patient by placing a suitable length of carrier into the tip of a hollow needle and then placing a stylet into the needle. The needle may be inserted into a patient and then pulled back over the stylet leaving the carrier in place. For methods of administration see, for example, A. van't Riet et al., Int. *J. Radiation Oncology Biol. Phys.,* Vol. 24, pages 555–558, 1992, hereby incorporated by reference.

Embodiments of the invention will be further illustrated with reference to the accompanying drawings, in which.

Figure 1:
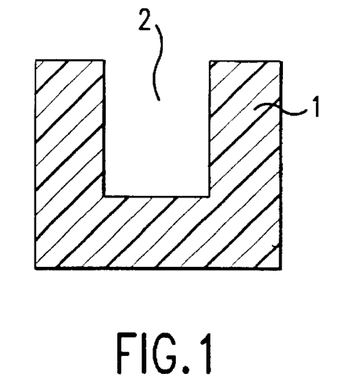
FIG. 1 is a schematic drawing of a cross-section through one embodiment of a carrier according to the invention.

FIG. 1 illustrates a carrier 1 of roughly square cross-section provided with a groove 2 in one side. The groove 2 runs along the longitudinal axis of the carrier 1.

Figure 2:
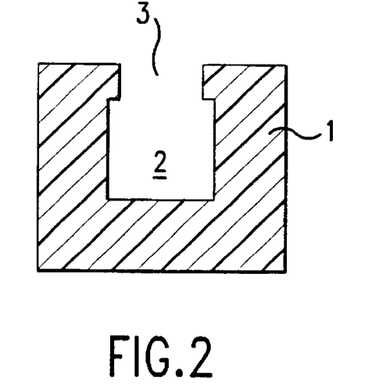
FIG. 2 is a schematic drawing of a cross-section through another embodiment of a carrier according to the invention.

FIG. 2 illustrates an alternative embodiment of a carrier 1 according to the invention. The opening 3 of the groove 2 is slightly narrower than the groove itself. A suitably sized source may be "clipped" into the carrier by pushing it through the opening and into the groove.

Figure 3:
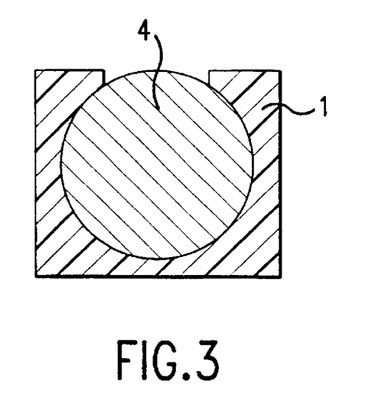
FIG. 3 is a schematic drawing of a cross-section through one embodiment of a carrier and a radioactive source according to the invention.

FIG. 3 illustrates the carrier 1 of FIG. 1 after a radioactive source 4 in the form of a seed has been heated and placed therein according to the first method of the invention. The source 4 has caused the carrier material to melt or soften and so deform around the source.

Figure 4:
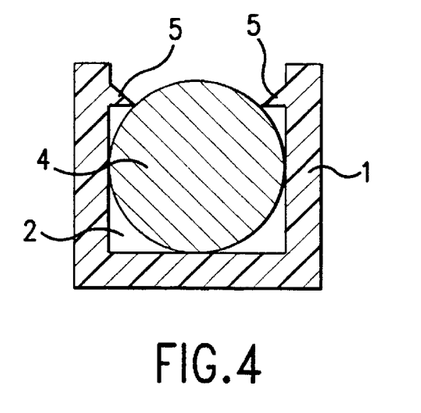
FIG. 4 is a schematic drawing of a cross-section through another embodiment of a carrier and a radioactive source according to the invention.

FIG. 4 illustrates an alternative embodiment of a carrier 1 with a radioactive source 4 in place. The source has been pushed into the groove 2 in the carrier past the lips 5 and the lips serve to hold the source in place.

Figure 5:
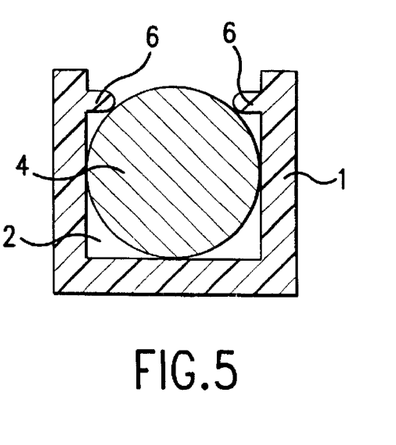
FIG. 5 is a schematic drawing of a cross-section through another embodiment of a carrier and a radioactive source according to the invention.

FIG. 5 illustrates another alternative embodiment of a carrier 1 with a radioactive source 4 in place. In this embodiment, protrusions in the form of knobs 6 serve to hold the seed in place.

Figure 6:
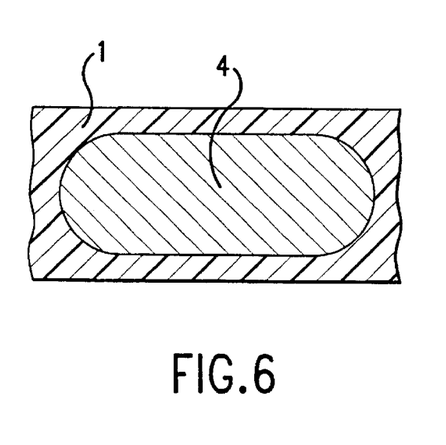
FIG. 6 is a section along part of the longitudinal axis of one embodiment of a radioactive member according to the invention.

FIG. 6 illustrates a longitudinal section through part of a radioactive member according to the invention. The radioactive source 4 has its longitudinal axis substantially aligned with that of the carrier 1.

Figure 7:
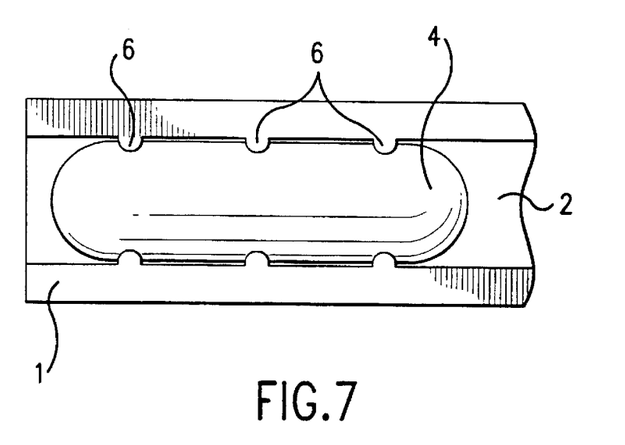
FIG. 7 is a schematic drawing of the top view of another embodiment of a carrier and radioactive source according to the invention.

FIG. 7 illustrates the top view of the carrier 1 and radioactive source 4 of FIG. 5. The source 4 is held in place in the groove 2 of the carrier 1 by 3 pairs of knobs 6. The pairs of knobs are spaced longitudinally along the groove 2.

Figure 8:
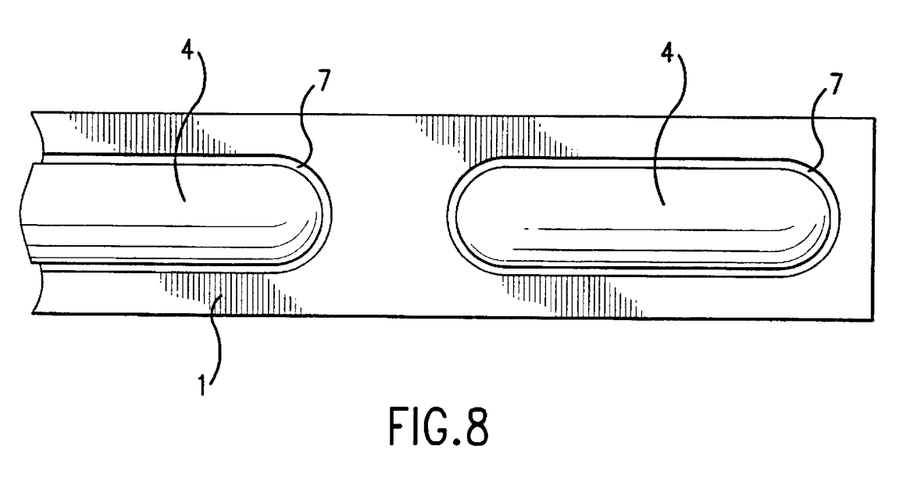
FIG. 8 is a schematic drawing of the top view of another embodiment of a carrier and radioactive source according to the invention and FIG. 9 is a schematic drawing of a cross-section through another embodiment of a carrier and radioactive source according to the invention.

FIG. 8 illustrates the top view of a further carrier 1 of the invention. The radioactive sources 4 are in a series of discrete openings 7 which are spaced along the longitudinal axis of the carrier 1 and substantially parallel to it. The sources may be held in place by use of a suitable adhesive or resin, or by provision of a coating, for example of Vicryl braid.

Figure 9:
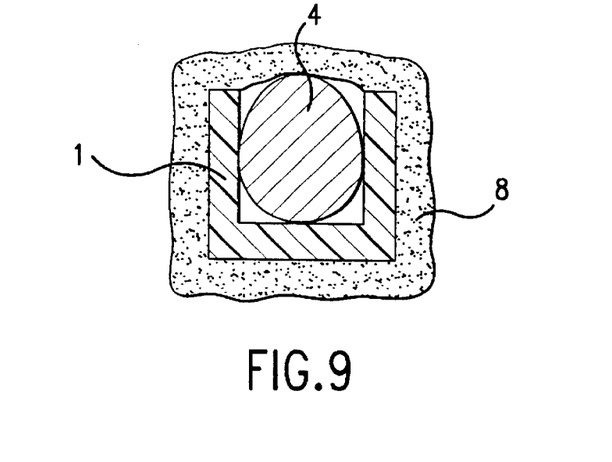

FIG. 9 illustrates a carrier 1 with a radioactive source 4 in place in a groove therein. The source is held in place by a coating 8 which encases the carrier 1. The coating may, for example, be in the form of a Vicryl braid.

Figure 10:
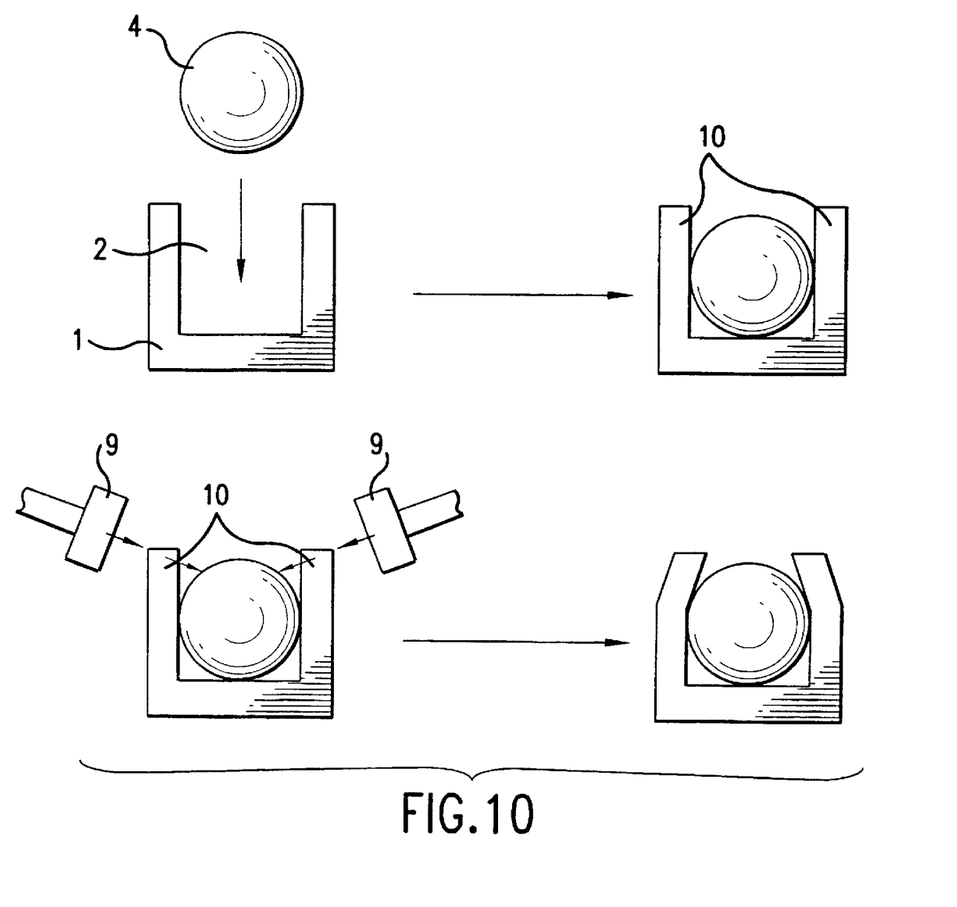
FIG. 10 illustrates in schematic form one method for the manufacture of a radioactive member of the invention.

FIG. 10 illustrates in schematic form two steps involved in one method for the manufacture of a radioactive member according to the invention. A carrier 1 and a radioactive source 4 are provided and in a first step the source is inserted into a groove 2 in the carrier 1. The groove 2 is large enough for the source to be placed therein without the need for any heating or deformation of the carrier 1. In a second step, heated plates 9 are applied to the portions 10 of the carrier 1 directly adjacent to the opening of the groove 2 such that the top portions 10 are deformed sufficiently around the source 4 to hold it in place in the groove 2 on cooling.

Figure 11A:
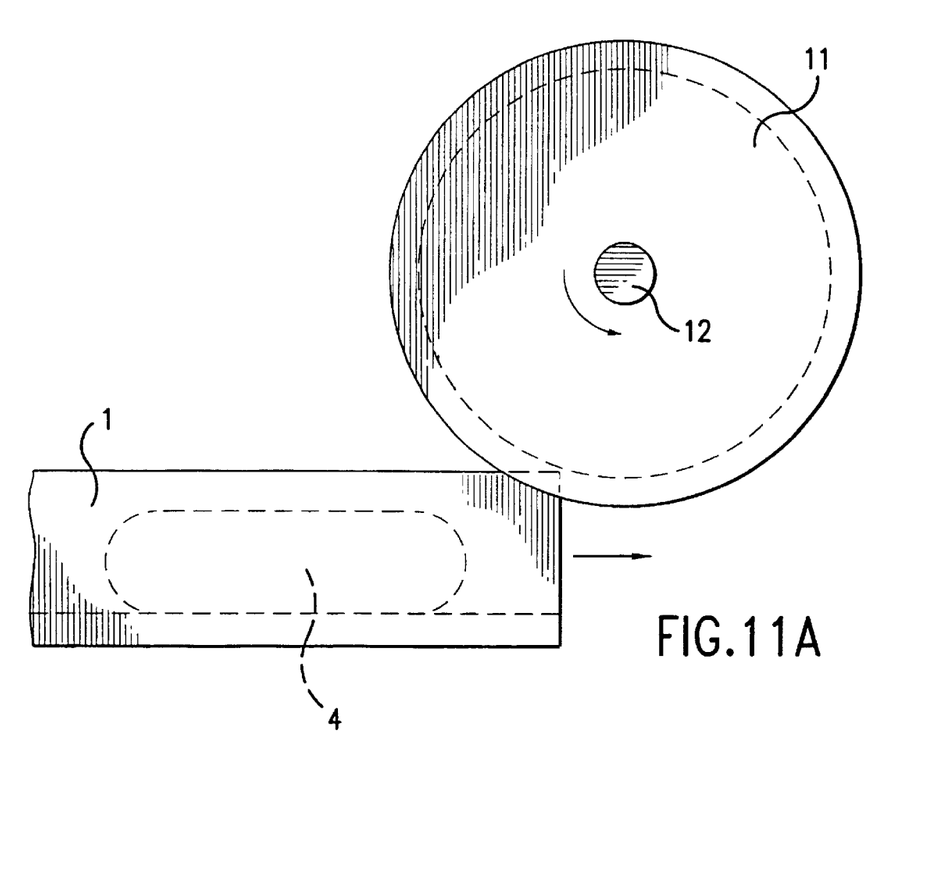
FIGS. 11A and B illustrate in schematic form another method for the manufacture of a radioactive member of the invention.
Figure 11B:
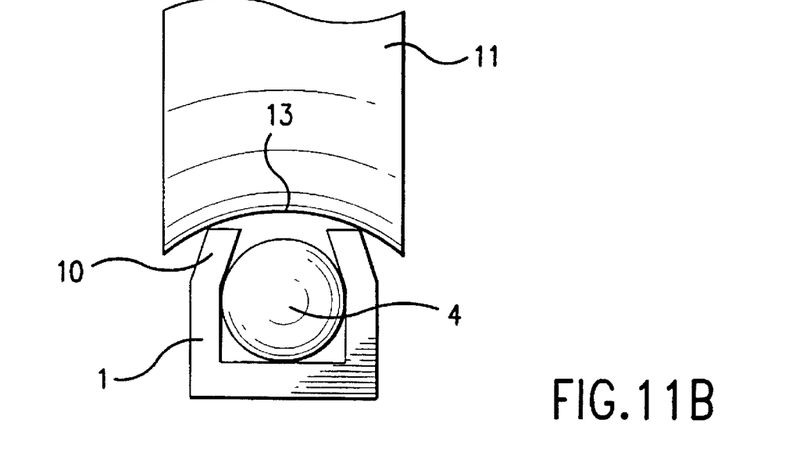

FIG. 11 illustrates in schematic form a further method for the manufacture of a radioactive member according to the invention. FIG. 11A shows in longitudinal section a source 4 in place in the groove of a carrier 1. The carrier moves into contact with a heated rotating roller 11, which rotates about an axis 12. The arrows indicate the direction of motion of the carrier and of rotation of the roller 11. The heated roller contacts the edges of the groove, causing them to soften or melt and then deform around the source 4 to hold it in place in the carrier. FIG. 11B shows an end view of the apparatus of FIG. 11A. A source 4 is in place in the groove 2 of a carrier 1. The concave surface 13 of the edge of the heated roller 11 contacts the top portions 10 of edges of the groove. The edges of the groove are thus pushed together such that the source 4 is held in place.

Figure 12:
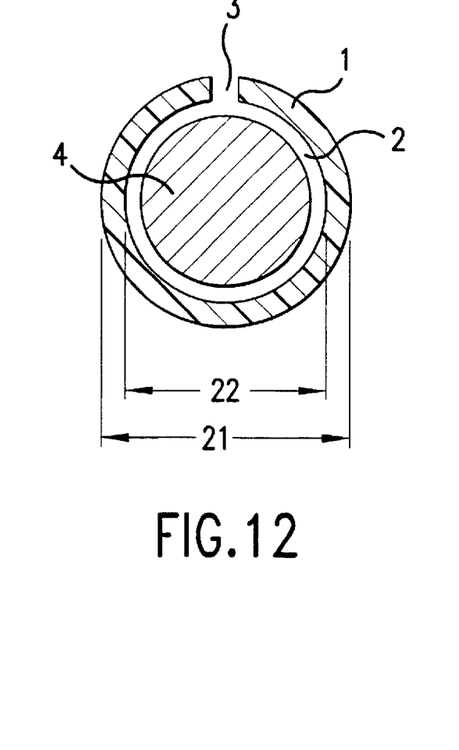
FIG. 12 is a schematic drawing of a cross section through another embodiment of a carrier according to the invention.

FIG. 12 illustrates a carrier such as that described in Example 1. In particular, it shows a carrier 1 of substantially circular cross-section provided with a longitudinal opening 3 leading into a groove 2. The source 4 may be inserted into the carrier by pushing it through the opening and into the groove. The carrier has an outside diameter 21 of approximately 0.102 cm (0.04 inches) and an inside diameter 22 approximately corresponding to that of the outside diameter of the source.

Figure 13:
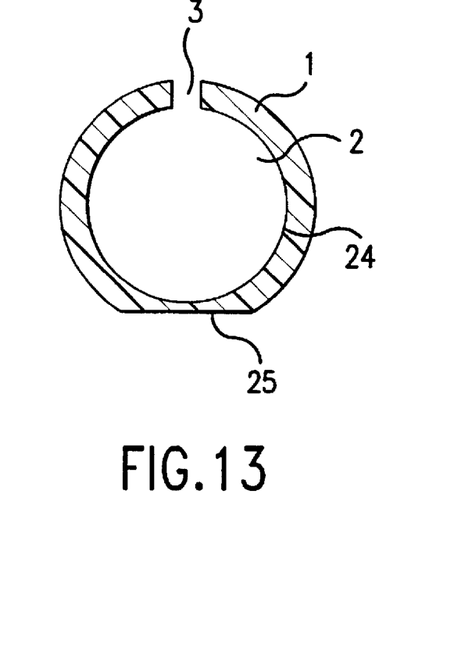
FIG. 13 is a schematic drawing of a cross section through another embodiment of a carrier according to the invention.

FIG. 13 illustrates a carrier 1 of substantially circular cross-section, having one flat surface 25 in its outer shape. In this embodiment, the opening 3, leading into the groove 2, is in a position diametrically opposed to the flat surface of the carrier. This feature enables orientation of the strand during manufacture; if, for example, the flat surface was held in place, the opening would be in a position opposite to the flat surface. The shape of the inner portion of the tube 24 is substantially circular.

Figure 14:
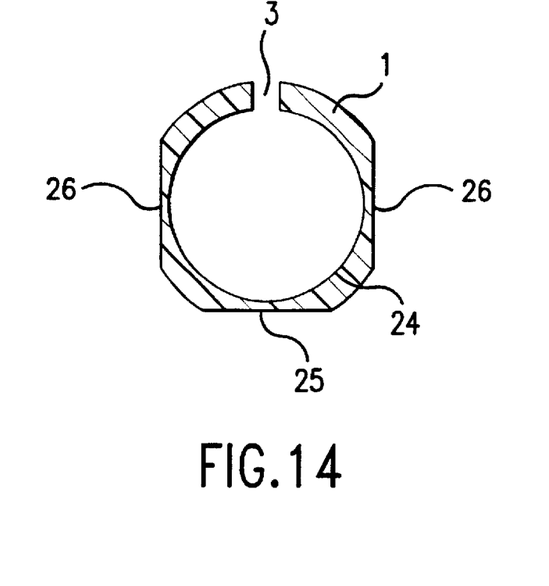
FIG. 14 is a schematic drawing of a cross section through another embodiment of a carrier according to the invention.

FIG. 14 illustrates a carrier 1 of substantially circular cross-section, having one flat surface 25 diametrically opposed to the opening 3 with two other flat surfaces 26 on either side of that surface 25. The shape of the inner portion of the tube 24 is substantially circular.

Figure 15:
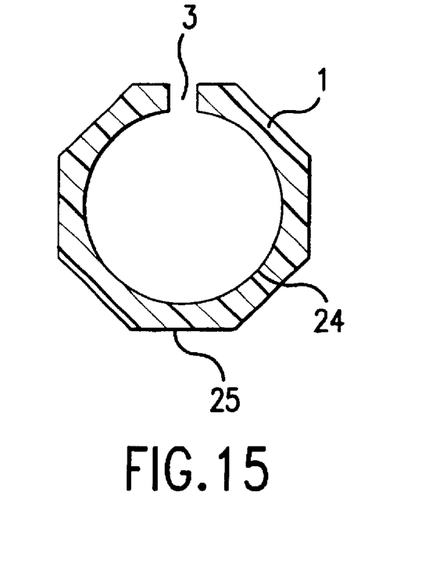
FIG. 15 is a schematic drawing of a cross section through another embodiment of a carrier according to the invention.

FIG. 15 illustrates a cross section of a carrier 1 having an outer shape which is substantially octagonal. An longitudinal opening 3 is position opposite one of the flat surfaces 25. The inner shape 24 is substantially circular.

The invention is further described with reference to the following non-limiting example.

EXAMPLE 1

A tube of poly L-lactide having an outside diameter of 0.102 cm (0.040 inches) and approximately 8 cm in length was made by machining down a larger piece of extruded polymer tubing. A slit along the long axis of the tubing was cut through the side wall. The slit was opened and 5 dummy seeds (approximately 4.5 mm long with a diameter of 0.8 mm) were placed within the void of the tube's inner diameter.

It was confirmed that the 8 cm long strand containing 5 seeds could pass through a Mannan needle.

What is claimed is:

1. A radioactive member for use in brachytherapy comprising an essentially stiff elongate, single stranded bioabsorbable carrier material with a plurality of spaced slots therein in which a plurality of radioactive sources are disposed therein.

2. The radioactive member of claim 1 wherein the radioactive sources are radioactive seeds.

3. The radioactive member of claim 1 wherein the carrier material includes poly(glycolic acid), poly(lactic acid), a polyester amide of glycolic or lactic acid, or a polydioxanone.

4. The radioactive member of claim 1 wherein the carrier material has a substantially circular cross section.

5. The radioactive member of claim 1 characterised in that the cross section of the carrier has at least one flat surface.

6. The radioactive member of claim 1 wherein the carrier has a substantially polygonal cross-section.

7. The radioactive member as claimed in claim 1 wherein the carrier includes ultrasound reflecting particles or bubbles of gas.

8. A radioactive member of claim 1 loaded onto a wheel or a jig.

9. A radioactive member of claim 8 wherein the wheel or jig is shielded.

10. A method for the production of a radioactive member for use in brachytherapy comprising an elongate, single stranded bioabsorbable carrier material with spaced radioactive sources disposed therein, said method comprising the steps of:
   a) providing an elongate essentially stiff single stranded bioabsorbable carrier material,
   b) providing a plurality of radioactive sources,
   c) heating the radioactive sources to a temperature above the melting or softening temperature of the carrier material,
   d) placing the heated sources sequentially or concurrently onto the carrier material in a predetermined pattern whereby the carrier material melts or deforms around each source, and
   e) cooling the carrier material such that is solidifies or hardens about each source so as to securely retain each source in place.

11. The method of claim 10 wherein the sources are radioactive seeds.

12. A method for the production of a radioactive member for use in brachytherapy comprising an elongate, single stranded bioabsorbable carrier material with spaced radioactive sources disposed therein, said method comprising the steps of:
   a) providing an elongate essentially stiff single stranded bioabsorbable carrier material which is at a temperature above its melting or softening temperature,
   b) providing a plurality of radioactive sources,
   c) placing the sources sequentially or concurrently onto the carrier material in a predetermined pattern whereby the carrier material melts or deforms around each source, and p1 d) cooling the carrier material such that it solidifies or hardens about each source so as to securely retain each source in place.

13. The method of claim 12 wherein the sources are radioactive seeds.

14. The method of claim 12 further comprising the step of heating the radioactive sources to a temperature above the melting or softening point of the carrier material prior to placing onto the carrier material.

15. A method for the production of a radioactive member for use in brachytherapy comprising an elongate, single stranded essentially stiff bioabsorbable carrier material with spaced radioactive sources disposed therein, said method comprising the steps of:
   a) providing an elongate single stranded bioabsorbable carrier material having a longitudinal groove therein,
   b) providing a plurality of radioactive sources,
   c) placing the sources sequentially or concurrently into the groove in the carrier material such that each source is securely retained in a slot within the groove.

16. The method of claim 15 wherein the sources are radioactive seeds.

17. The method of claim 15 wherein the sources are retained in the groove using a biocompatible adhesive or resin.

18. The method of claim 15 wherein the sources are retained in the groove by means of one or more rails, lips, tabs or knobs.

19. A method for the production of a radioactive member for use in brachytherapy comprising an elongate, single stranded essentially stiff bioabsorbable carrier material with spaced radioactive sources disposed therein, said method comprising the steps of:
   a) providing an elongate single stranded bioabsorbable carrier material having a plurality of discrete openings spaced longitudinally therein,
   b) providing a plurality of radioactive sources,
   c) placing the sources sequentially or concurrently into the openings in the carrier material such that each source is securely retained within the openings.

20. The method of claim 19 wherein the sources are radioactive seeds.

21. The method of claim 19 wherein the sources are retained in the openings using a biocompatible adhesive or resin.

22. The method of claim 19 wherein the sources are retained in the openings by means of one or more rails, lips, tabs or knobs.

23. A method of treatment of a condition which is responsive to radiation therapy which comprises the placement of a radioactive member comprising an essentially stiff elongate, single stranded bioabsorbable carrier material with spaced radioactive sources disposed in slots at or adjacent the site to be treated within a patient for a sufficient period of time to deliver a therapeutically effective dose.

24. The method of treatment of claim 23 wherein the condition is cancer.

25. The method of claim 24 wherein the radioactive member is visualized using a suitable imaging technique in connection with real-time dosimetry equipment.

26. The method of claim 25 wherein the imaging technique comprises ultrasound imaging.

27. A method for the production of a radioactive member for use in brachytherapy comprising an elongate, single stranded essentially stiff bioabsorbable carrier material with spaced radioactive sources disposed therein, said method comprising the steps of:
   a) providing an elongate single stranded bioabsorbable carrier material having a longitudinal groove therein,
   b) providing a plurality of radioactive sources,
   c) placing the sources sequentially or concurrently into the groove in the carrier material, and
   d) providing means to apply an external force to deform the edges of the groove around the sources such that each source is securely retained in the groove.

28. The method of claim 27 wherein the sources are radioactive seeds.

29. The method of claim 27 wherein the means comprise a heated plate, baffle, flange, wheel or roller.

30. A method as claimed in claim 29 wherein the means comprise a concave surface.

31. A radioactive member for use in brachytherapy comprising an elongate, single-stranded, essentially stiff bioabsorbable carrier material with one or more slots therein in which one or more radioactive sources are disposed in a spaced apart fashion.

* * * * *

UNITED STATES PATENT AND TRADEMARK OFFICE
CERTIFICATE OF CORRECTION

PATENT NO.     : 6,679,824 B1        Page 1 of 1
DATED          : January 20, 2004
INVENTOR(S)    : Jay Reed et al.

It is certified that error appears in the above-identified patent and that said Letters Patent is hereby corrected as shown below:

<u>Column 13,</u>
Line 49, after the word "and" delete "p1"

Signed and Sealed this

Twenty-fifth Day of May, 2004

JON W. DUDAS
*Acting Director of the United States Patent and Trademark Office*